(12) United States Patent
Maurette

(10) Patent No.: US 9,211,211 B2
(45) Date of Patent: Dec. 15, 2015

(54) FEMALE POSTERIOR WALL PROSTHESIS

(76) Inventor: Neil Luke Maurette, Calgary (CA)

( * ) Notice: Subject to any disclaimer, the term of this patent is extended or adjusted under 35 U.S.C. 154(b) by 770 days.

(21) Appl. No.: 12/698,790

(22) Filed: Feb. 2, 2010

(65) Prior Publication Data

US 2011/0190574 A1    Aug. 4, 2011

(51) Int. Cl.
| | |
|---|---|
| A61F 6/06 | (2006.01) |
| A61F 6/08 | (2006.01) |
| A61F 2/50 | (2006.01) |
| A61H 19/00 | (2006.01) |
| A61F 5/41 | (2006.01) |
| A61F 2/00 | (2006.01) |

(52) U.S. Cl.
CPC ... *A61F 6/08* (2013.01); *A61F 2/50* (2013.01); *A61F 5/41* (2013.01); *A61H 19/50* (2013.01); *A61F 2/005* (2013.01); *A61H 2201/165* (2013.01)

(58) Field of Classification Search
CPC .............. A61F 6/06; A61F 6/08; A61H 19/00
USPC .......... 600/29–32, 37, 38, 186, 222; 128/830
See application file for complete search history.

(56) References Cited

U.S. PATENT DOCUMENTS

| | | | |
|---|---|---|---|
| 3,640,284 A | | 2/1972 | DeLangis |
| 4,048,985 A | | 9/1977 | Sasse |
| 4,241,912 A | | 12/1980 | Mercer et al. |
| 4,895,363 A | | 1/1990 | Plevnik et al. |
| 5,256,123 A | | 10/1993 | Reinbolt |
| 5,460,165 A | * | 10/1995 | Mayes ........................ 600/186 |
| 5,785,640 A | * | 7/1998 | Kresch et al. .................. 600/29 |
| 6,418,930 B1 | * | 7/2002 | Fowler .......................... 128/830 |
| 6,672,996 B2 | | 1/2004 | Ross |
| 2008/0009775 A1 | | 1/2008 | Murison |
| 2009/0069634 A1 | * | 3/2009 | Larkin .......................... 600/222 |
| 2009/0281373 A1 | | 11/2009 | Mark |

* cited by examiner

*Primary Examiner* — Christine H Matthews

(57) ABSTRACT

A prosthesis comprising a pancake-shaped body, a narrowed neck and a flared flattened handle sized and shaped to shield the posterior vaginal wall from frictional contact during coitus. The pancake-shaped body unfurls during insertion and provides for the prosthesis to be retained within the vagina and the flared flattened handle prevents the prosthesis from entering the vagina during insertion of the prosthesis or during coitus. This prosthesis decreases the volume of the vagina and decreases the area of the vaginal opening providing a non-surgical, cost-effective solution to tightening a woman's vagina. The posterior vaginal wall prosthesis enables women who have larger vaginas to use tampons.

18 Claims, 4 Drawing Sheets

FEMALE POSTERIOR WALL PROSTHESIS

CROSS REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

1. Field

This application relates generally to medical devices, particularly to a prosthesis constructed to duplicate the posterior vaginal wall.

2. Prior Art

After an episiotomy, vaginoplasty or vaginal tear, the remaining healed scar on the posterior vaginal wall can be painful or the area on the posterior vaginal wall can be hypersensitive. There is a need for a sensitive area covering device that can be worn on the posterior vaginal wall during coitus to reduce the friction on this area to help with the hypersensitivity in this area. Standard medical practice when performing an episiotomy is to cut from the introitus towards and into the perineum. These areas are the site of various surgical and non-surgical traumas comprising tears, occlusions, sutures, scars, sores, genital warts and genital herpes all of which can cause the posterior vaginal wall, the introitus and the perineal area to be hypersensitive.

In addition, a woman's vagina and vaginal entrance naturally differ in size from person to person. Factors such as aging, overstretching from childbirth or sexual activities can further cause the vagina and vaginal entrance to lose elasticity. To help tighten her vagina, a woman has a few options available to choose from. These options have varying degrees of success and risk.

Since early times, some women have used creams that claim to tighten the vagina. Evidence shows that noticeable tightening effects of these ointments are considered to be ineffective. Application of the cream to the interior walls of the vagina is difficult, embarrassing, and must be properly timed to correspond with sexual intercourse. Some of the creams contain benzocaine, alum or petroleum jelly, none of which are recommended for being inserted into the vagina.

Another prior art alternative is to perform an alum douche. Alum douches are not recommended by doctors, can be irritating and are associated with increased risk of pelvic and vaginal infections. Alum is an astringent that acts to contract the vagina walls, but there is no way to judge how long the constriction will last nor a way to control the extent of tightening.

Performing exercises designed to strengthen pubococcygeal muscles, such as the exercises developed by Dr. Arnold Kegel of the University of California, is a doctor recommended way to exercise the vaginal muscles to tighten the vagina. For those who find it difficult to identify these muscles, biofeedback systems can be useful. These muscles can also be exercised using various vaginal exercise devices (U.S. Pat. No. 4,241,912 to Mercer et al. (1980), U.S. Pat. No. 4,048,985 to Sasse (1977), U.S. Pat. No. 4,895,363 to Plevnik et al. (1990), U.S. Pat. No. 5,256,123 to Reinbolt (1993), to name a few). One disadvantage to these exercise methods is that it takes a long time, an average of 6 to 12 weeks, to see results, so one must be dedicated to maintain the muscle development program long enough for it to be of benefit. In addition, like any muscle, if the muscles are not continually worked, the pubococcygeal muscles will lose their strength. Another disadvantage is that to be of benefit during sexual intercourse, the female must consciously flex her interior muscles, thus taking away from her ability to relax and enjoy the act of intercourse itself.

Electrotherapy of the vagina such as described in U.S. Pat. No. 3,640,284 to De Langis (1972), reproduces the physical and chemical phenomenon connected with normal muscular work. A small electronic probe is placed in the vagina and painless, low frequency electrical currents cause contractions of the vaginal muscles. Alternatively, the vaginal muscles can be exercised with attractive magnets such as described in U.S. Pat. No. 6,672,996 to Ross et al. (2004). Unfortunately, both of these methods are expensive and not viable for use in home conditions.

Vaginoplasty is a surgical procedure that helps tighten the vaginal muscles as well as the supporting tissues of the vaginal wall. Any excess vaginal mucosal tissue is excised or removed with a laser. The result is an immediate decrease in the size of vaginal muscles. This is a costly procedure, and has the following risks: problems with anesthesia, bleeding, hematoma, infection with swelling, soreness and tenderness and post operative scarring. There is also the risk of losing sensitivity due to complications within the vaginal wall area and muscles.

U.S. Publication No. 2009/0281373, by Mark, describes a sexual aid device which is inserted within a human female's vagina to provide a sensation of increased fullness to the female and a sensation of increased tightness and friction to a penis of a human male during sexual intercourse.

Deficiencies in Mark's sexual aid device and method are as follows:

(a) Mark's device is not engineered or designed for shielding the posterior vaginal wall, the introitus or the perineum while in use (use here comprises sitting, walking, normal daily activities and coitus). Mark's device neglects to cover a broad area comprising the posterior vaginal wall, the introitus and the perineum, thus exposing women, who experience hypersensitivity, to frictional contact in these areas. The posterior vaginal wall, the introitus and the perineum are often the location of hypersensitivity, including but not limited to, tears, occlusions, sutures, scars, sores, warts and herpes. Furthermore, Mark's device guarantees frictional contact along the full extent of the posterior vaginal wall, the introitus and the perineum when the device is attached to a penis via a ring or a condom. This frictional contact further irritates hypersensitive areas.

(b) Mark's device is not engineered or designed to be used outside of coitus. His device is not designed to be retained exclusively by the vagina at all times. Within the vagina, Mark's device is designed with only one mechanism of retention, a bulbous head. When a female uses Mark's device, and is in a standing position, the device is susceptible to movement by gravity such that the bulbous head drops towards the vaginal entrance. Mark's embodiment that has an anal penetrator serves as a second means of retention, however, this form of retention complicates daily restroom activities and may otherwise not be suitable for all day wear. Mark's device is not designed to be comfortably worn all day and all night.

(c) Mark's device does not have shape geometry that allows the device to seat itself when being inserted into the vagina and to remain seated during use without penetrating the anus. When Mark's device is positioned in a single orifice, his device is not self-locating, is not self-retaining, does not remain in a user defined position and does not resist rotation. Mark's device does not have a mechanism to unfurl which serves to pull the device into the vagina when it passes the vaginal entrance muscles nor does his device have shape and geometry to prevent the device from wholly entering the vagina while being inserted and while in use. Mark's device does not have features which retain the device in a user-defined, pre-determined position inside and outside of the vagina.

(d) Mark's device is not engineered or designed to be exclusively retained by the vagina to enable a female to use a blood collection device, such as a tampon. Furthermore, his device does not function to support a method of transdermal medication delivery.

(e) Mark's device is not designed to accommodate insertable and removable electronic devices. His device has built-in electronic devices which increase the manufacturing costs, limit the end users' options, and render Mark's device not easily recyclable.

(f) Mark's embodiments that are manufactured from a single material stretch the introitus muscles when the device is inserted. To minimize stretching of the introitus muscles, Mark does have an embodiment that is cylindrically collapsible for insertion into the vagina, however, this embodiment requires at least two different types of materials and a more complex manufacturing process which complicates recycling of the device. Mark's device does not take advantage of an engineered shape that is simple to manufacture and that can be rolled by hand into a narrow cylinder for easy insertion into the vagina without stretching the introitus muscles.

Therefore, there is a need for some women for a non-surgical, cost-effective solution to shield at all times a sensitive area on the posterior vaginal wall, the introitus and the perineal area, to restore the sensation of a tightened vaginal entrance and to enable women with larger vaginas to use a tampon. In this regard, the posterior vaginal wall prosthesis substantially fulfills this need. The posterior vaginal wall prosthesis according to the present invention substantially departs from the conventional concepts and designs of any prior art.

Objects and Advantages

Accordingly, several objects and advantages of the posterior vaginal wall prosthesis are:
(a) to provide a prosthesis which is self-retaining, hands-free and ergonomic which shields against frictional contact on the posterior vaginal wall, the introitus and the perineal area;
(b) to provide a prosthesis which effectively decreases the volume of the vagina and decreases the area of the vaginal opening, thus providing a non-surgical, cost-effective solution to giving a woman the sensation of a tightened vagina;
(c) to provide a prosthesis which will allow couples to achieve the desired fit and desired sensations during sexual intercourse, decreasing the need to look outside the relationship for the desired fit and sensations, thus decreasing the transmission of AIDS and other sexually transmitted diseases or infections;
(d) to provide a prosthesis which increases sensations for the male partner by applying more pressure around the penis;
(e) to provide a prosthesis which prevents tampons from falling out of larger vaginas, thus enabling the use of tampons;
(f) to provide a prosthesis which has design features to ensure that the prosthesis remains in place while the vagina is being penetrated by foreign objects;
(g) to provide a prosthesis that rolls up into a cylindrical tube-like shape that allows for easy insertion into the female vagina, the vaginal entrance muscles not needing to expand to accommodate insertion of the prosthesis;
(h) to provide a prosthesis which naturally unfurls after insertion to provide the necessary tension in its unfurled state to self-retain, to self-locate and to remain in place in the vagina;
(i) to provide a prosthesis that has a flared flattened handle that resides on the outside of the vaginal entrance that follows the natural contours of the perineal area protecting this area;
(j) to provide a prosthesis that has a flared flattened handle that serves to prevent the entire device from entering the vagina;
(k) to provide a prosthesis which is retained simultaneously both inside and outside of the vagina;
(l) to provide a prosthesis which resists rotation after being inserted into the vagina.

Further objects and advantages will become apparent from a consideration of the ensuing description and drawings.

DRAWINGS

Figures

DRAWINGS

Figure 1:
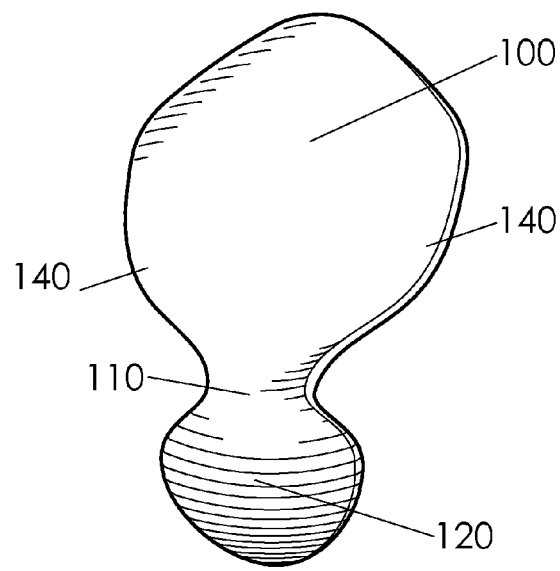
FIG. 1 is an isometric view from above of the posterior vaginal wall prosthesis with a mid-section bulb in accordance with one embodiment.

Reference Numerals 100 pancake-shaped body
110 narrowed neck
120 flared flattened handle
130 mid-section bulb
140 protruding side wing
240 body retainer
250 handle retainer
260 body finger hole
270 handle finger hole
280 texture
290 recess
310 combined retainer
610 posterior vaginal wall
620 posterior fornix
630 perineum
640 introitus

DETAILED DESCRIPTION

FIGS. 1-6—First Embodiment

Figure 2:
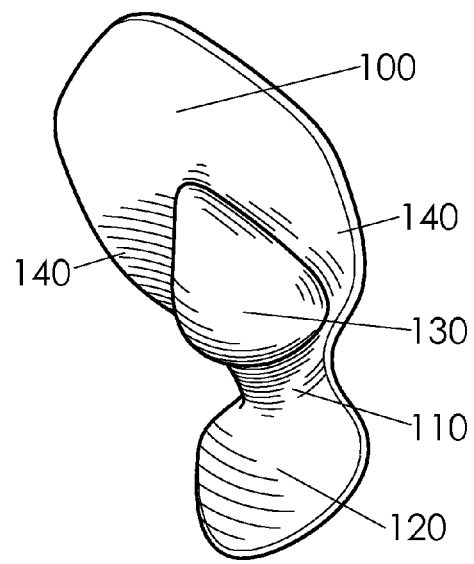
FIG. 2 is an isometric view from below of the posterior vaginal wall prosthesis of FIG. 1.
Figure 3:
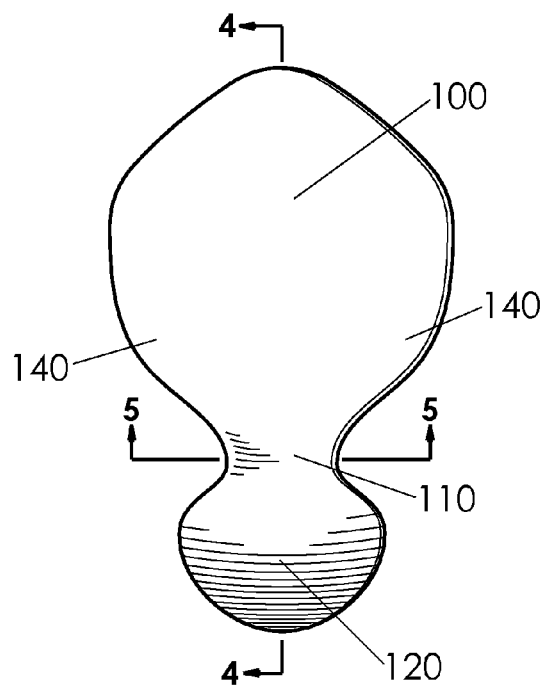
FIG. 3 is a top view of the posterior vaginal wall prosthesis of FIG. 1.
Figure 4:
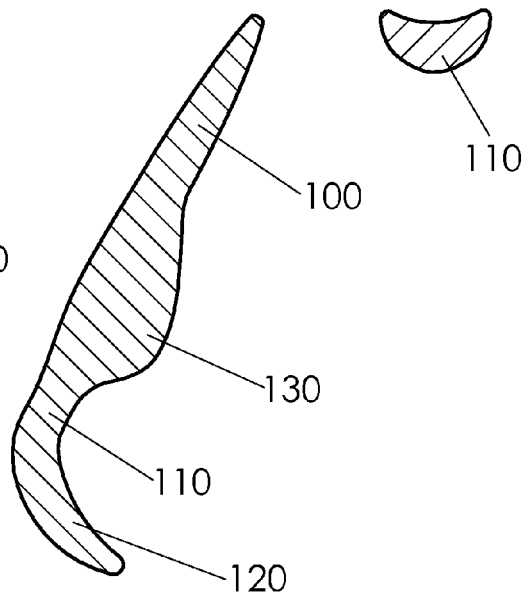
FIG. 4 is a cross sectional view taken along line 4-4 of the posterior vaginal wall prosthesis of FIG. 3.
Figure 5:
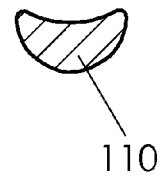
FIG. 5 is a cross sectional view taken along line 5-5 of the posterior vaginal wall prosthesis of FIG. 3.
Figure 6:
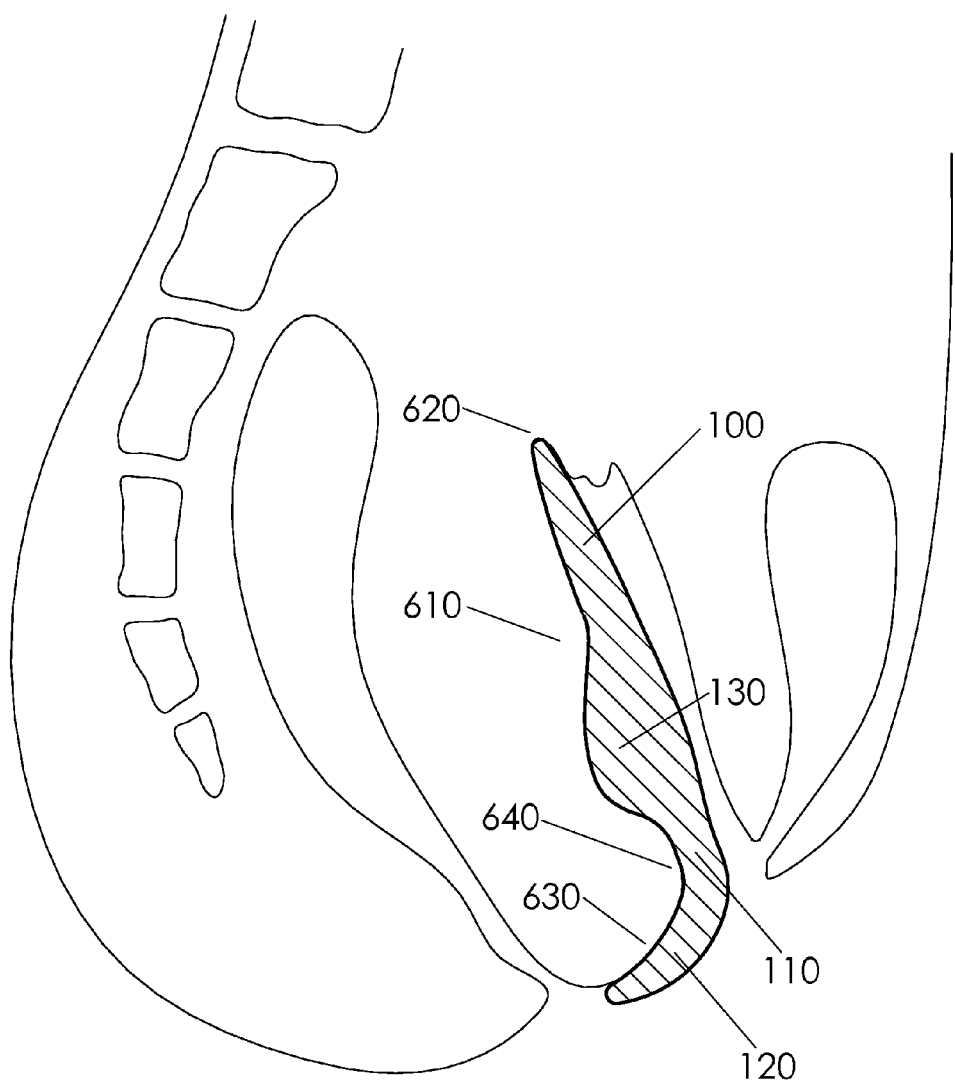
FIG. 6 is a sagittal view showing the posterior vaginal wall prosthesis of FIG. 1 in position in the vaginal passage of a human female.
Figure 7:
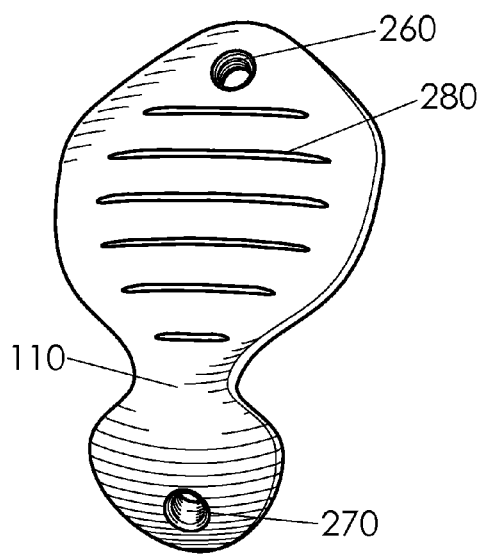
FIG. 7 is an isometric view from above of the posterior vaginal wall prosthesis in accordance with a second embodiment.
Figure 8:
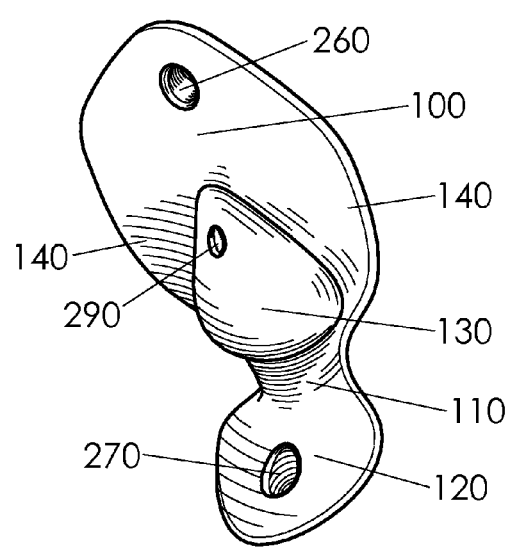
FIG. 8 is an isometric view from below of the posterior vaginal wall prosthesis of FIG. 7.
Figure 9:
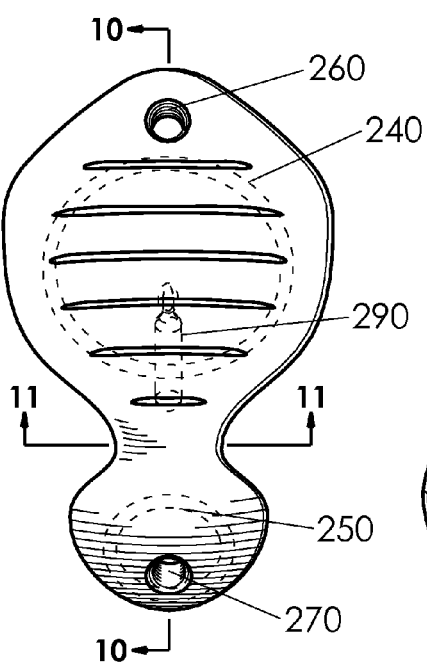
FIG. 9 is a top view of the posterior vaginal wall prosthesis of FIG. 7.
Figures 10, 11:
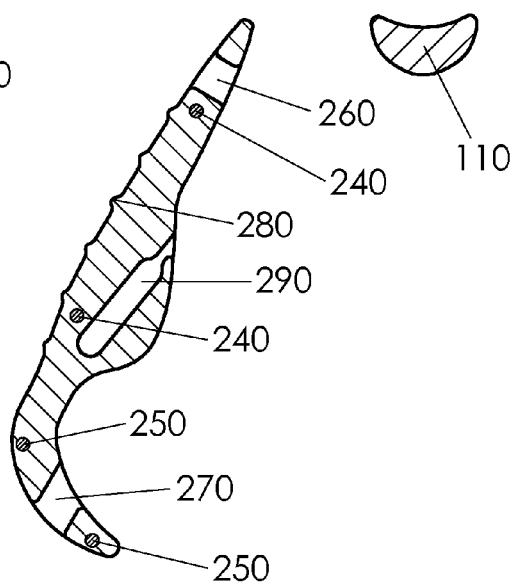
FIG. 10 is a cross sectional view taken along line 10-10 of the posterior vaginal wall prosthesis of FIG. 9.
FIG. 11 is a cross sectional view taken along line 11-11 of the posterior vaginal wall prosthesis of FIG. 9.
Figure 12:
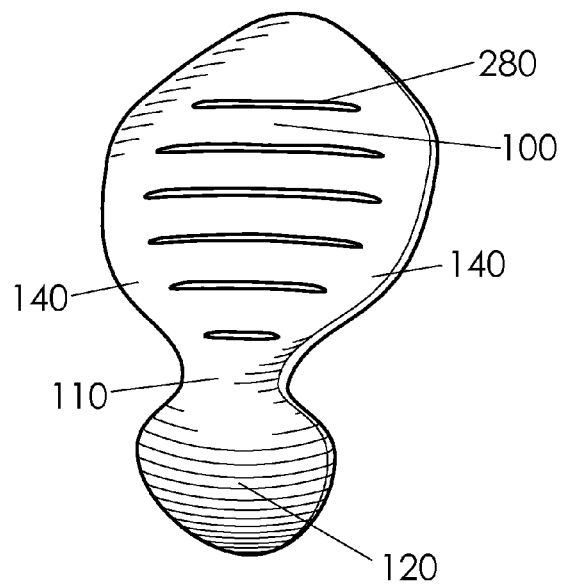
FIG. 12 is an isometric view from above of the posterior vaginal wall prosthesis in accordance with a third embodiment.
Figure 13:
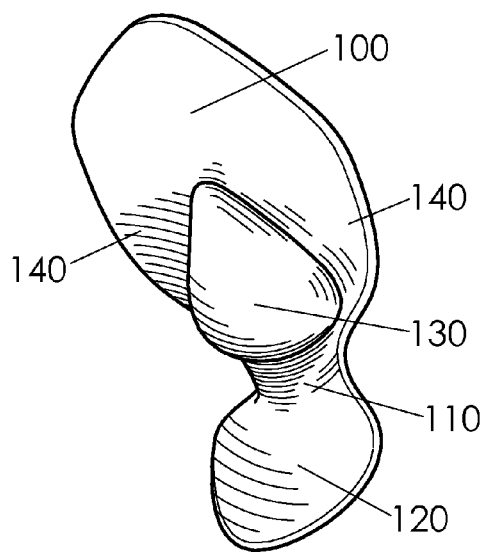
FIG. 13 is an isometric view from below of the posterior vaginal wall prosthesis of FIG. 12.
Figure 14:
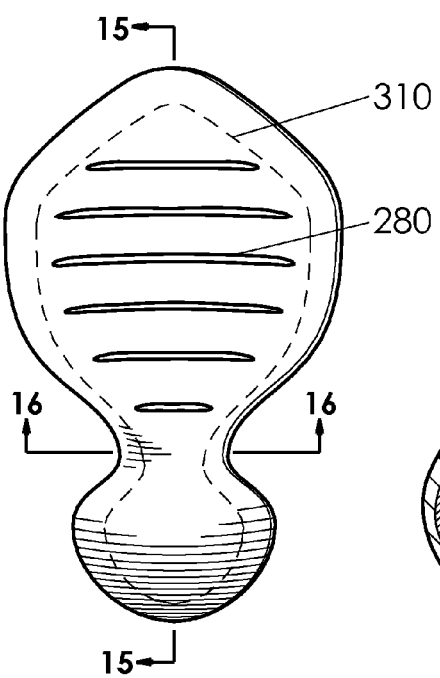
FIG. 14 is a top view of the posterior vaginal wall prosthesis of FIG. 12.
Figure 15:
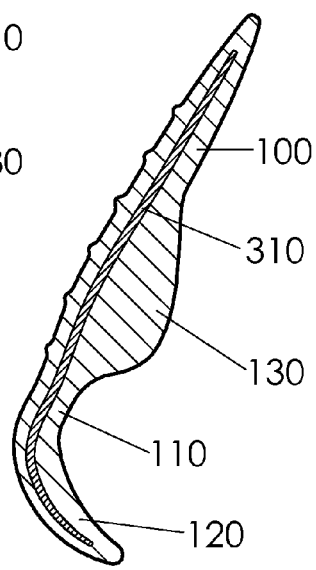
FIG. 15 is a cross sectional view taken along line 15-15 of the posterior vaginal wall prosthesis of FIG. 14.
Figure 16:
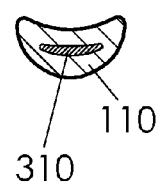
FIG. 16 is a cross sectional view taken along line 16-16 of the posterior vaginal wall prosthesis of FIG. 14.

One embodiment of the posterior vaginal wall prosthesis which resembles a paddle with a curved handle is illustrated in FIGS. 1-5. This embodiment comprises a pancake-shaped body 100, a narrowed neck 110, a flared flattened handle 120, and a mid-section bulb 130. The pancake-shaped body 100 includes two protruding side wings 140, 140. The narrowed neck 110 connects the pancake-shaped body 100 to the flared flattened handle 120 as illustrated in FIG. 1. This embodiment comprises a flexible, resilient, unitary structure wherein the pancake-shaped body 100 and the flared flattened handle 120 are disposed in divergent relation with an included angle in between. Within this included angle, the tear-drop shaped mid-section bulb 130 is positioned at the base of the pancake-shaped body 100 near the narrowed neck 110 with the largest part of the bulb placed closest to the narrowed neck 110 as shown in FIG. 2. The posterior vaginal wall prosthesis is sized and configured to be placed in a human female vagina as shown in FIG. 6 so that the end of the pancake-shaped body 100 is disposed towards the posterior fornix 620 of the vagina, the mid-section bulb 130 is positioned to contact the posterior vaginal wall 610, the narrowed neck 110 is at the introitus 640 and the flared flattened handle 120 points towards the perineum 630. It is important to note that the narrowed neck 110 is crescent-shaped to allow sexual intercourse when the prosthesis is thus positioned in a vagina. The cross section of the narrowed neck 110 is illustrated in FIG. 5.

The preferred material for the manufacture of this embodiment is a medical-grade silicone or an elastomeric gel with a durometer measuring between 15-25 on the Shore 0 scale of hardness. Preferred elastomeric gels to be used are described in U.S. Pat. No. 5,807,360 to Shubin (1998). This embodiment of the posterior vaginal wall prosthesis can be made with any other material that comprises the following characteristics. The material should be soft and flexible and deformable by human fingers. The material should have elastic memory to prevent permanent deformation and allow the prosthesis to naturally unroll after insertion into the vagina. The material should also be stable and capable of multiple washings without deterioration. The material should also have the density and tactile feel of human flesh and be capable of readily transmitting vibrations and heat throughout the material.

The posterior vaginal wall prosthesis is molded using conventional liquid injection molding techniques and technologies.

Operation—FIGS. 1-6—First Embodiment

Starting at one of the protruding side wings 140 and ending with the opposite protruding side wing 140, the pancake-shaped body 100 is rolled up with the mid-section bulb 130 on the outside. The rolled up pancake-shaped body 100 is then inserted into the vagina until the narrowed neck 110 is positioned at the introitus 640 and the flared flattened handle 120 resides on the exterior of the vagina, adjacent the perineum 630 (see placement in human female vaginal passage in FIG. 6). Once inside the vaginal cavity, due to the prosthesis material's natural tendency to return to its original shape, the prosthesis will unroll. However, complete unfurling is not necessary for the prosthesis to function as intended. Slight minor displacements for comfort can be performed by adjusting the flared flattened handle 120. In this position, the prosthesis reduces the volume of the internal cavity and reduces the area of the vaginal entrance. In addition, various narrowed neck geometrical configurations can emulate a larger male sex organ. The mid-section bulb 130 and the shape of the pancake-shaped body 100 act as a retention means to retain the prosthesis within the vagina. The shape of the flared flattened handle 120 acts as a prevention means to prevent the flared flattened handle 120 from entering the vagina.

To remove the prosthesis, the flared flattened handle 120 is clasped and the prosthesis is gently pulled out of the vagina. Due to the shape and the deformability of the pancake-shaped body 100, the prosthesis will naturally fold the wings 140 to allow the prosthesis to be removed. The prosthesis can then be cleaned and reused.

To use the posterior vaginal wall prosthesis with a tampon, the prosthesis is placed in position as described above and the tampon is next inserted into place following tampon insertion instructions. The tampon is then removed and changed as needed. The prosthesis can be removed, washed and reinserted as needed.

Description—FIGS. 7-11—Second Embodiment

Another embodiment of the posterior vaginal wall prosthesis is shown in FIGS. 7-11. The embodiment shown in FIGS. 7-11 comprises texture 280 on the non-bulb side, a deformable body retainer 240 embedded in the pancake-shaped body 100, a deformable handle retainer 250 embedded in the flared flattened handle 120, finger holes 260 and 270, and a recess 290 in the mid-section bulb 130. Texture 280 is provided on the pancake-shaped body 100 on the non-bulb side and serves to act as a further means of retention by creating a higher friction surface. This surface texture 280 serves to enhance stimulation to the male sex organ and effectively duplicate the texture of the posterior vaginal wall 610. Note that localized texture 280 or texture 280 on the entire surface of the prosthesis aids to keep tampons in place. The deformable body retainer 240 applies continuous pressure in an attempt to flatten out the pancake-shaped body 100 in the vagina after insertion. The shape of the pancake-shaped body 100, the mid-section bulb 130, the body retainer 240, and the texture 280 serve to hold the posterior vaginal wall prosthesis within the vagina. The shape of the flared flattened handle 120 and the handle retainer 250 reduce the tendency for the prosthesis to enter the vagina during sexual intercourse. If and/or when using lubricants, the prosthesis may become slippery; the body finger hole 260 and the handle finger hole 270 serve as a means to locate and more easily grasp the prosthesis.

The recess 290 can house a vibrating and/or pulsating device commonly known as a "bullet" vibrator (not shown). This comprises an electrically-driven motor with an eccentrically-mounted load, encapsulated in a generally cylindrical casing with a rounded tip. Such a "bullet" may be powered and controlled remotely and may or may not have electrical cabling, or may be internally battery-powered. Some versions merely vibrate; others have a range of selectable pulsating modes. With the correct choice of materials, the vibrations and/or pulses will be transmitted throughout the prosthesis. Alternatively, the recess 290 can house an electrically-powered warming device, applied in the same manner as is the pulsating/vibrating mechanism.

The preferred material for the embodiment of the posterior vaginal wall prosthesis illustrated in FIGS. 7-11 is the same as the preferred material for the first embodiment, with a different material required for the body retainer 240 and the handle retainer 250.

The body retainer 240 and the handle retainer 250 are preferably constructed from a similar material used for the first embodiment, albeit more rigid. The preferred material for the manufacture of the retainers is a medical grade silicone with a durometer measurement of between 25-75 on the Shore A scale of hardness. The retainers can also be manufactured from any material with elastomeric properties that can be manually stressed to deform easily. The material must be flexible so that human fingers can roll the prosthesis into a tube-like shape prior to insertion into the vagina and yet resilient enough to flex back to, or close to, its original shape. Other common shape memory materials that can be used for the retainers comprise: plastics, rubbers, nylons, and polyurethanes. Round retainers 240 and 250 are illustrated in the embodiment of FIGS. 7-11, however, rectangular, triangular, or any other shape can be over-molded into the prosthesis to facilitate the same flexural function.

The retainers themselves can be manufactured using industry standard liquid injection molding technologies and techniques. However, the retainers can also be common, standard, off the shelf, ready-made silicone O-ring retainers as shown in the embodiment of FIGS. 7-11.

The prosthesis with retainers of FIGS. 7-11 is manufactured using conventional liquid injection over-molding techniques and technologies.

Operation—FIGS. 7-11—Second Embodiment

To operate the embodiment from FIGS. 7-11, if so desired, the user first inserts a "bullet" or a warming device into the recess 290 of the prosthesis, securing the "bullet" or warming device in the recess 290 with a pressure fit. Then, the embodiment of FIGS. 7-11 is operated in the same way as the first embodiment of FIGS. 1-6. In addition, the user can grasp the handle finger hole 250 of the posterior vaginal wall prosthesis embodiment of FIGS. 7-11 to pull the prosthesis out of the vagina. The body retainer 240 will deform due to its elastic nature to allow removal. A string can also be affixed to the handle finger hole 270 to aid in the removal of the prosthesis.

If the prosthesis slips entirely into the vagina, the handle finger hole 270 and the body finger hole 260 serve as a means to locate, grasp and remove the prosthesis. This is especially useful if additional lubricants are used.

Description—FIGS. 12-16—Third Embodiment

The embodiment of FIGS. 12-16 illustrates an embodiment of the prosthesis with a combined retainer 310. The combined retainer 310 is a unitary retainer that combines the body retainer 240 and the handle retainer 250 and passes through the narrowed neck 110. The combined retainer has the same purpose as the separate retainers, serving to unroll the prosthesis after being rolled up and inserted into the vagina. The combined retainer 310 also holds the pancake-shaped body 100 in place within the vagina and prevents the flared flattened handle 120 from entering the vagina before, during and after coitus.

The preferred material for the manufacture of this embodiment is the same material as the material described for the first embodiment shown in FIGS. 1-5. The combined retainer 310 is made of a similar and more rigid material to facilitate the added flexural function. The preferred material for the manufacture of the combined retainer 310 is that of the body retainer 240 material described for the embodiment of FIGS. 7-11.

The combined retainer 310 is manufactured using conventional liquid injection molding techniques and technologies. The prosthesis with the combined retainer is manufactured using conventional liquid injection over-molding techniques and technologies.

Operation—FIGS. 12-16—Third Embodiment

The embodiment of FIGS. 12-16 is operated in the same manner as the embodiment illustrated in FIGS. 1-5 described above.

CONCLUSION, RAMIFICATIONS AND SCOPE

Accordingly, the reader will see that the posterior vaginal wall prosthesis can be used to shield the posterior vaginal wall, the introitus and the perineal area. Furthermore, the prosthesis provides women with a new, highly effective, economical, non-surgical means to reduce the volume of the vagina and decrease the area of the vaginal entrance. The prosthesis is simple to use, is easily adjusted for comfort and provides pleasure to both the female and the male partner.

While the above figures and descriptions contain many specificities, the reader should not construe these as limitations on the scope of the invention, but merely as exemplifications of several preferred embodiments thereof. Various other embodiments are possible. For example, different flexible and resilient materials can be used for the prosthesis and retainers. The pancake-shaped body and flared flattened handle can be diamond-shaped, rectangular, triangular, round or have various other shapes. The thicknesses of the pancake-shaped body and the mid-section bulb can be varied. The flared flattened handle can have finger holes or not. Optionally, the flared flattened handle may further comprise a means of anal penetration for an added means of retention. The narrowed neck can have different thicknesses and can be shaped to cover more or less surface area of the introitus resulting in varying degrees of sensations of vaginal tightness. The mid-section bulb can take on different shapes and be placed higher or lower on the pancake-shaped body. The mid-section bulb can be eliminated. The body retainer and the handle retainer can also have different shapes, vary in cross-section and be made of different materials. The texture can take other forms including dimples, small finger-like projections, or wavy contours. The texture can be localized or on the entire surface of the prosthesis. Pigments, scents, anti-bacterial agents or medication can be added to the material that comprises the prosthesis. The prosthesis can be shaped and sized for use in other sexually receptive orifices. Therefore, the reader is requested to determine the full scope of the invention by the appended claims and their legal equivalents, and not by the examples given.

I claim:

1. An insertable and removable prosthetic article, comprising:

a. a pancake-shaped body,
   said pancake-shaped body having a posterior side,
   said pancake-shaped body having a longitudinal axis,
   said posterior side of the pancake-shaped body being configured to be positioned along a posterior wall of a human female vagina,
   said pancake-shaped body being sized and shaped to substantially shield the posterior vaginal wall,
   said pancake-shaped body having a plurality of protruding side wings,
   said plurality of protruding side wings being sized and shaped to curl into a cylinder,
   said plurality of protruding side wings being sized and shaped to unfurl,
   said plurality of protruding side wings protruding perpendicularly to said longitudinal axis,
   said pancake-shaped body being sized and shaped to be retained within the vagina,
   said pancake-shaped body comprising a resiliently deformable elastomeric material,
b. a flared flattened handle,
   said flared flattened handle being configured to reside on an exterior of the vagina,
   said flared flattened handle having a proximal end and a distal end,
   the distal end extending towards the posterior side of said pancake-shaped body,
   said flared flattened handle initially flaring substantially outward in shape from the proximal end as a distance from the proximal end increases,
   said flared flattened handle being sized and shaped to substantially shield a female perineum,
   said flared flattened handle being sized and shaped to prevent said flared flattened handle from entering the vagina,
   said flared flattened handle being sized and shaped to permit vaginal penetration by a foreign object when said pancake-shaped body is in place inside the vagina,
c. a narrowed neck,
   said narrowed neck connecting said pancake-shaped body to said flared flattened handle,
   said narrowed neck having said longitudinal axis,
   said longitudinal axis extending from said narrowed neck through said pancake-shaped body,
   said narrowed neck being configured to be positioned at an entrance of the vagina when said pancake-shaped body is positioned in place in the vagina,
   said narrowed neck being sized and shaped to permit vaginal penetration by the foreign object when said pancake-shaped body is in place inside the vagina,
   said narrowed neck being sized and shaped to taper from said flared flattened handle,
   said narrowed neck being sized and shaped to taper from said pancake-shaped body,
   said pancake shaped body flaring substantially outward in shape from said narrowed neck as a distance along said longitudinal axis increases and
   whereby a female can shield the posterior vaginal wall, the vaginal entrance and the perineum from frictional contact at all times—and can be enabled to retain tampons.

2. The insertable and removable prosthetic article of claim 1, wherein said pancake-shaped body further comprises a mid-section bulb,
   said mid-section bulb having a tear-drop shape,
   said mid-section bulb being attached to said posterior side of said pancake-shaped body,
   said mid-section bulb being positioned on said pancake-shaped body to have the largest end of the tear-drop shape closest to said narrowed neck, and said mid-section bulb being sized and shaped to retain said pancake-shaped body inside the vagina.

3. The insertable and removable prosthetic article of claim 1, comprising a resiliently deformable elastomeric material.

4. The insertable and removable prosthetic article of claim 3, further comprising a transdermal material.

5. The insertable and removable prosthetic article of claim 1, further comprising at least one externally accessible recess means.

6. The insertable and removable prosthetic article of claim 5, wherein the at least one externally accessible recess means is provided to receive a means of additional stimulation comprising at least one insertable device selected from the group consisting of vibration devices, pulsation devices, vibration and pulsation devices, and warming devices, whereby said means of additional stimulation is separable by hand from said insertable and removable prosthetic article and is electrically powered.

7. The insertable and removable prosthetic article of claim 1, further comprising a retaining means.

8. The insertable and removable prosthetic article of claim 7, wherein said retaining means comprises: at least one device selected from the group consisting of body retainers, handle retainers, combined retainers and anal penetrators, whereby said retaining means is a resilient internal skeleton.

9. The insertable and removable prosthetic article of claim 1, further comprising a textured surface.

10. A method of protecting a posterior vaginal wall, a vaginal entrance and
   a perineum of a human female, comprising:
   a. providing a posterior vaginal wall shield comprising
      a pancake-shaped body,
         said pancake-shaped body having a posterior side,
         said pancake-shaped body having a longitudinal axis,
         said posterior side of the pancake-shaped body being configured to be positioned along a posterior wall of a human female vagina,
         said pancake-shaped body being sized and shaped to substantially shield the posterior vaginal wall,
         said pancake-shaped body having a plurality of protruding side wings,
         said plurality of protruding side wings being sized and shaped to curl into a cylinder
         said plurality of protruding side wings being sized and shaped to unfurl,
         said plurality of protruding side wings protruding perpendicularly to said longitudinal axis,
         said pancake-shaped body being sized and shaped to be retained within the vagina,
         said pancake-shaped body comprising a resiliently deformable elastomeric material, a flared flattened handle,
         said flared flattened handle being configured to reside on an exterior of the vagina,
         said flared flattened handle having a proximal end and a distal end,
         the distal end extending towards the posterior side of said pancake-shaped body,
         said flared flattened handle initially flaring substantially outward in shape from the proximal end as a distance from the proximal end increases,
         said flared flattened handle being sized and shaped to substantially shield a female perineum, said flared flattened handle being sized and shaped to prevent said flared flattened handle from entering the vagina, said flared flattened handle being sized and shaped to permit vaginal penetration by a foreign object when said pancake-shaped body is in place inside the vagina, a narrowed neck, said narrowed neck connecting said pancake-shaped body to said flared flattened handle, said narrowed neck having said longitudinal axis, said longitudinal axis extending from said narrowed neck through said pancake-shaped body, said narrowed neck being configured to be positioned at an entrance of the vagina when said pancake-shaped body is positioned in place in the vagina, said narrowed neck being sized and shaped to permit vaginal penetration by the foreign object when said pancake-shaped body is in place inside the vagina, said narrowed neck being sized and shaped to taper from said flared flattened handle, said narrowed neck being sized and shaped to taper from said pancake-shaped body, said pancake shaped body flaring substantially outward in shape from said narrowed neck as a distance along said longitudinal axis increases, b. rolling said pancake-shaped body of said posterior vaginal wall shield into a cylinder that axially aligns said pancake-shaped body, said narrowed neck and said flared flattened handle, c. inserting said posterior vaginal wall shield into the vagina, until said narrowed neck is at the vaginal entrance and said flared flattened handle remains outside the vagina, adjacent to the perineum, d. letting said pancake-shaped body naturally unroll once clear of the vaginal entrance so that said pancake-shaped body is retained by the vaginal entrance, e. adjusting the placement of said posterior vaginal wall shield with said flared flattened handle, and whereby the female can shield the posterior vaginal wall, the vaginal entrance and the perineum from frictional contact at all times and can be enabled to retain a tampon.

11. The method of claim 10, wherein said posterior vaginal wall shield further comprises a mid-section bulb, said mid-section bulb having a tear-drop shape, said mid-section bulb being attached to said posterior side of said pancake-shaped body, said mid-section bulb being positioned on said pancake-shaped body to have the largest end of the tear-drop shape closest to said narrowed neck and said mid-section bulb being sized and shaped to retain said pancake-shaped body inside the vagina.

12. The method of claim 10, wherein said posterior vaginal wall shield further comprises a retaining means.

13. The method of claim 12, wherein said retaining means comprises at least one device selected from the group consisting of body retainers, handle retainers, combined retainers and anal penetrators, whereby said retaining means is a resilient internal skeleton.

14. The method of claim 10, wherein said posterior vaginal wall shield further comprises at least one externally accessible recess means.

15. The method of claim 14, wherein at least one electrically powered insertable device selected from the group consisting of vibrational devices, pulsation devices, vibrational and pulsation devices, and warming devices is inserted into the at least one externally accessible recess means, the at least one electrically powered insertable device is separable by hand from said posterior vaginal wall shield.

16. The method of claim 10, wherein said posterior vaginal wall shield further comprises a resiliently deformable elastomeric material.

17. The method of claim 16, wherein the material of said posterior vaginal wall shield comprises a transdermal material.

18. The method of claim 10, wherein said posterior vaginal wall shield further comprises a textured surface.

* * * * *